(12) United States Patent
Taylor, Jr.

(10) Patent No.: US 6,512,456 B1
(45) Date of Patent: Jan. 28, 2003

(54) MOBILE MEDICAL MONITORING DEVICE

(76) Inventor: John E Taylor, Jr., 19080 SW 44th St., Dunnellon, FL (US) 34432

( * ) Notice: Subject to any disclaimer, the term of this patent is extended or adjusted under 35 U.S.C. 154(b) by 0 days.

(21) Appl. No.: 09/707,716

(22) Filed: Nov. 7, 2000

Related U.S. Application Data

(63) Continuation-in-part of application No. 09/385,481, filed on Aug. 30, 1999, now Pat. No. 6,218,945, which is a continuation-in-part of application No. 09/229,023, filed on Jan. 12, 1999, now Pat. No. 6,160,481, which is a continuation-in-part of application No. 08/926,746, filed on Sep. 10, 1997, now Pat. No. 5,867,103.

(51) Int. Cl.[7] .............................................. G08B 23/00
(52) U.S. Cl. ...................... 340/573.1; 340/539; 604/156
(58) Field of Search .............................. 340/539, 573.1, 340/573.4, 825.49; 600/509, 529, 903, 904, 300, 301; 604/156, 140; 128/903, 904

(56) References Cited

U.S. PATENT DOCUMENTS

| | | | | |
|---|---|---|---|---|
| 5,204,670 A | * | 4/1993 | Stinton | 340/573.4 |
| 5,321,618 A | * | 6/1994 | Gessman | 128/904 |
| 5,652,570 A | * | 7/1997 | Lepkofker | 340/573.1 |
| 5,731,757 A | * | 3/1998 | Layson, Jr. | 340/573.4 |
| 5,827,180 A | * | 10/1998 | Goodman | 600/300 |
| 5,860,957 A | * | 1/1999 | Jacobnsen et al. | 604/156 |
| 5,944,659 A | * | 8/1999 | Flach et al. | 600/300 |
| 6,095,985 A | * | 8/2000 | Raymand et al. | 600/513 |
| 6,100,806 A | * | 8/2000 | Gaukel | 340/573.4 |
| 6,213,942 B1 | * | 4/2001 | Flach et al. | 600/300 |
| 6,334,778 B1 | * | 1/2002 | Brown | 434/258 |

* cited by examiner

*Primary Examiner*—Van Trieu

(57) ABSTRACT

A mobile monitoring device provides for measurement of a bodily function of a mobile monitored person while the mobile monitored person moves about during their daily activities. Various methods are explained to measure various bodily functions which may be employed with the mobile monitoring device. Means are provided for determining the onset of a medical crisis in the health of the mobile monitored person. A medical intervention may be employed in response to the detection of the onset of the medical crisis. A notification of an oversight authority may be employed in response to the detection of the onset of the medical crisis. Locational tracking provides for the oversight authority to quickly and efficiently dispatch medical assistance in response to the onset of the medical crisis. Historic preservation of the measurements of the bodily functions allow medical personnel to better prescribe a course of treatment to medical problems including following onset of the medical crisis. The oversight authority may also electronically inform friends and family members of the condition of the mobile monitored person as well as his or her location at any given time. This may include e-mail notification, telephonic notification as well as posting to an internet site where others, with approved access, may monitor the well being of the mobile monitored person. Tracking of a notification list of persons may be electronically maintained to ensure that all persons which the mobile monitored person wishes to have informed of his or her condition are so informed.

18 Claims, 6 Drawing Sheets

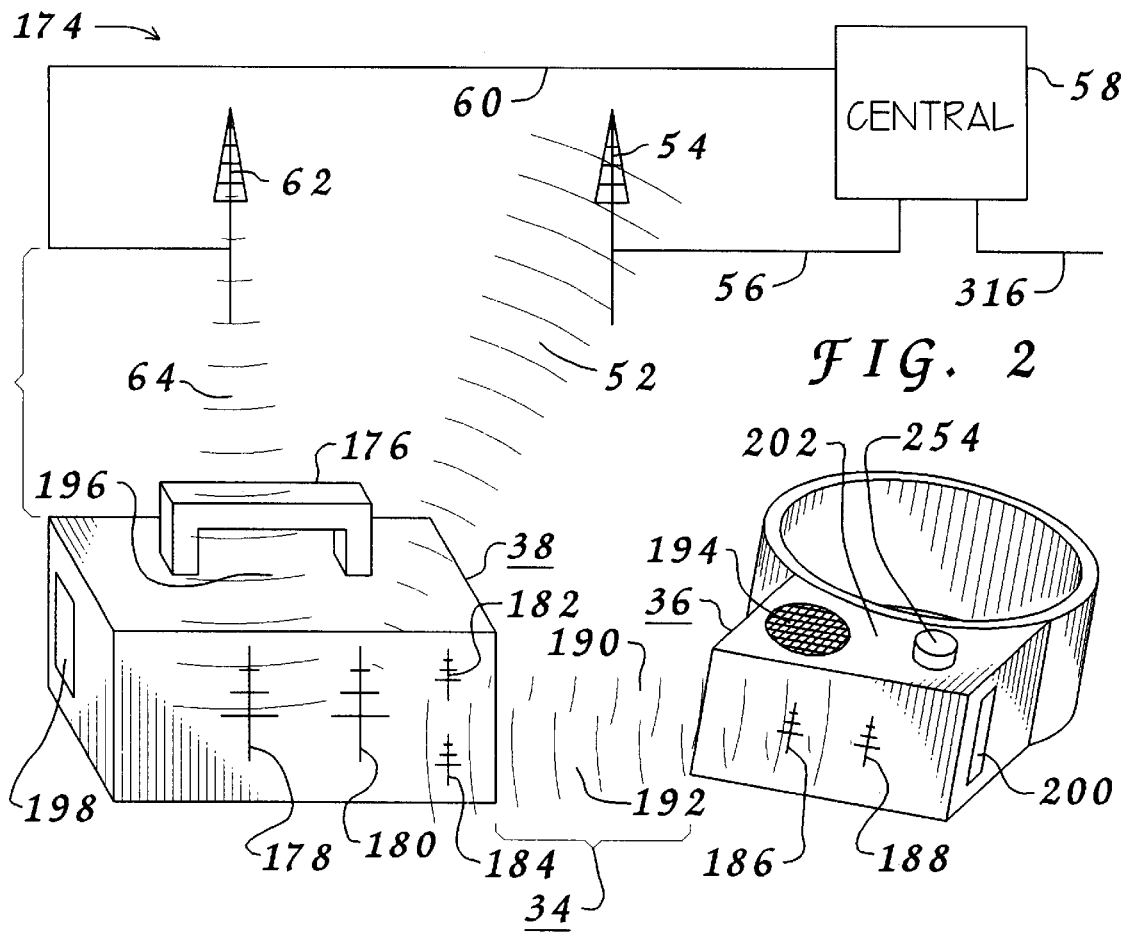
FIG. 2
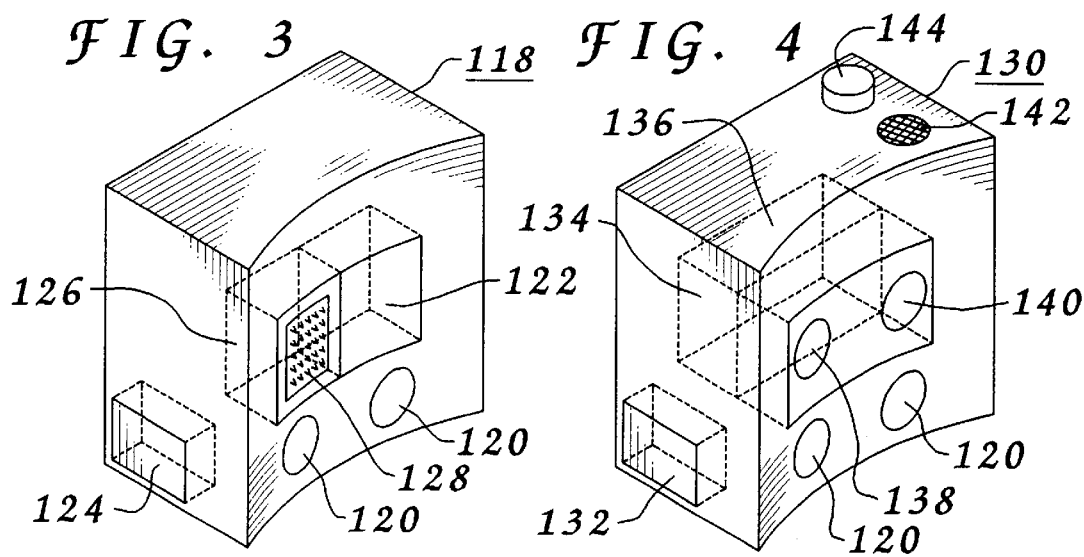
FIG. 3
FIG. 4

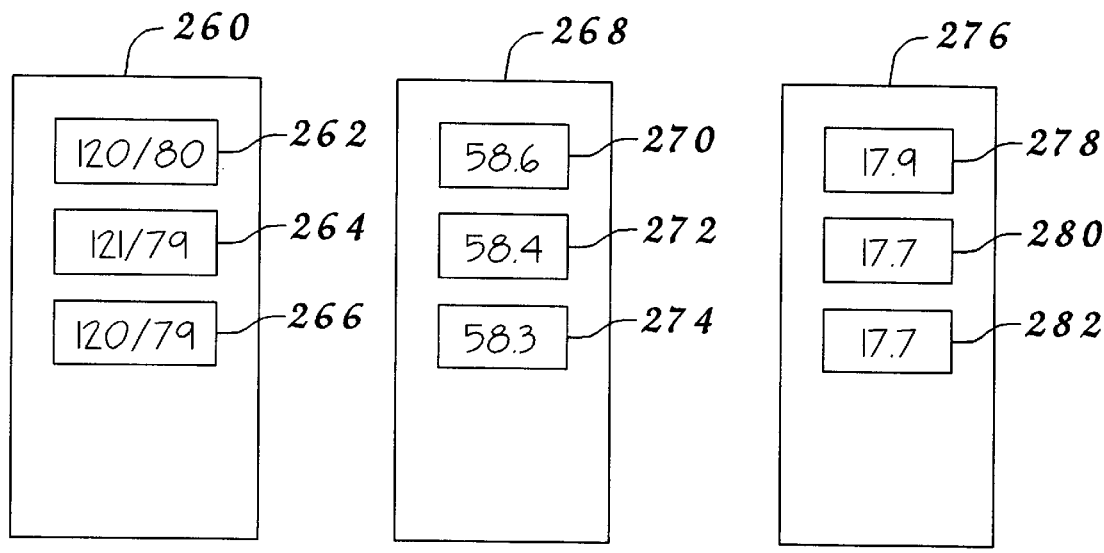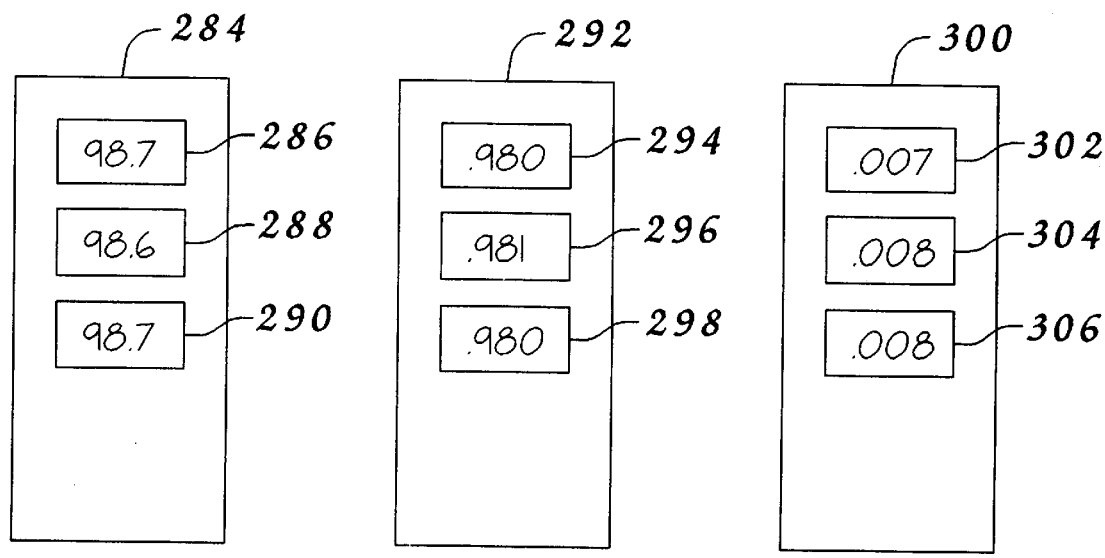

To: Ms. Sue Smith

Your father, Mr. John Smith, suffered a mild heart attack at 9:43 A.M. standard time on June 2, 2000.
He has been transported and admitted to General Hospital in Anycity Florida.
He is in stable condition, out of danger and resting comfortably. He will be held for testing for at least two days.
You may contact the hospital by calling 352-123-4567 or you may reach your fathers nursing station by calling 352-123-1234.
Your father Doctor is Dr. John Doe and he may be reached by calling 352-123-9876.
The hospitals visting hours are 8AM to 8PM. For additional information contact our secure Web site.

Enter Monitored Person's Identification Number _____

PASSWORD _____

312

MOBILE MEDICAL MONITORING DEVICE

CROSS-REFERENCE

This application is a continuation-in-part of Ser. No. 09/385,481 filed Aug. 30, 1999, entitled "Augmented Monitoring System", now U.S. Pat. No. 6,218,945, which is a continuation-in-part of Ser. No. 09/229,023 filed Jan. 12, 1999, entitled "Monitoring System", now U.S. Pat. No. 6,160,481, which is a continuation-in-part of U.S. Pat. No. 5,867,103, Ser. No. 08/926,746 filed Sep. 10, 1997, entitled "Monitored Person Tracking System". These applications are incorporated herein by this reference.

BACKGROUND

1. Field of the Invention

Generally, the invention relates to mobile monitoring devices which measure a bodily function. More specifically, the invention relates to such devices which measure a bodily function and take some action in the event that the measurement of the bodily function indicates that a medical crisis has begun.

2. Description of the Prior Art

Various equipment exists to measure various bodily functions of a monitored person. These devices include those which require manual manipulation by an operator in order to make their respective measurements as well as those which continually automatically make their respective measurements. These devices include those which are restricted to a location of operation during their operation as well as those which are mobile during their operation.

It is known, as exampled by in a hospital setting, to combine such monitoring of a bodily function with notification of an oversight authority, as exampled by personnel at a nursing station.

It is known to provide for locational tracking of a mobile person to provide for detached personnel to monitor the location of the mobile person, as exampled by some probation tracking systems.

It is known to provide for various medical interventions, either of a medication or of an electrical shock, in order to stabilize, or otherwise improve, the health of a person suffering a medical crisis.

Heretobefore it has been unknown to combine these various functions into a single overall system. As such, it may be appreciated that there continues to be a need for a monitoring system which may measure a bodily function of a mobile person during their routine movement during their activities of daily living while ascertaining if the mobile person suffers the onset of a medical crisis and automatically institute a course of action in response to the onset of that medical crisis. The present invention substantially fulfills these needs.

SUMMARY

In view of the foregoing limitations in monitoring systems, your applicant has devised a monitoring system having means to measure a bodily function of a mobile monitored person, means to determine if a medical crisis has commenced and means to respond to the onset of that medical crisis to provide assistance to the mobile monitored person.

My invention resides not in any one of these features per se, but rather in the particular combinations of them herein disclosed and it is distinguished from the prior art in these particular combinations of these structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important therefore, that the claims be regarded as including such equivalent constructions insofar as they do not depart from the spirit and scope of the present invention.

It is therefore a primary object of the present invention to provide for a mobile monitoring of a bodily function of a mobile monitored person while that person moves freely about during their daily activities.

Other objects include;
  a) to provide for making a determination if the bodily function being measured reaches a threshold indicative of onset of a medical crisis.
  b) to provide for performing an automated medical intervention in response to onset of the medical crisis.
  c) to provide for the medical intervention to involve introduction of a medication into the system of the mobile monitored person.
  d) to provide for the medical intervention to involve introduction of an electrical shock upon the system of the mobile monitored person.
  e) to provide for a timed delay of activation of the medical intervention to allow the mobile monitored person to cancel introduction of the medical intervention.
  f) to provide for making a notification of an oversight authority in response to onset of the medical crisis.
  g) to provide for locational tracking of the mobile monitored person and to include informing the oversight authority of the location of the mobile monitored person in response to onset of the medical crisis.
  h) to provide for a preservation of the measurements of the bodily function for historic usage.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein;

FIG. 2 is an illustration of another embodiment of a system having features of the present invention.

FIG. 3 is a perspective view of an embodiment of a monitoring device.

FIG. 4 is a perspective view of another embodiment of a monitoring device.

FIG. 10a through FIG. 10f are plan views of representations of various databases.

FIG. 11 is a representation of an e-mail transmission.

FIG. 12 is a representation of a web site transmission.

DESCRIPTION

Figure 1:
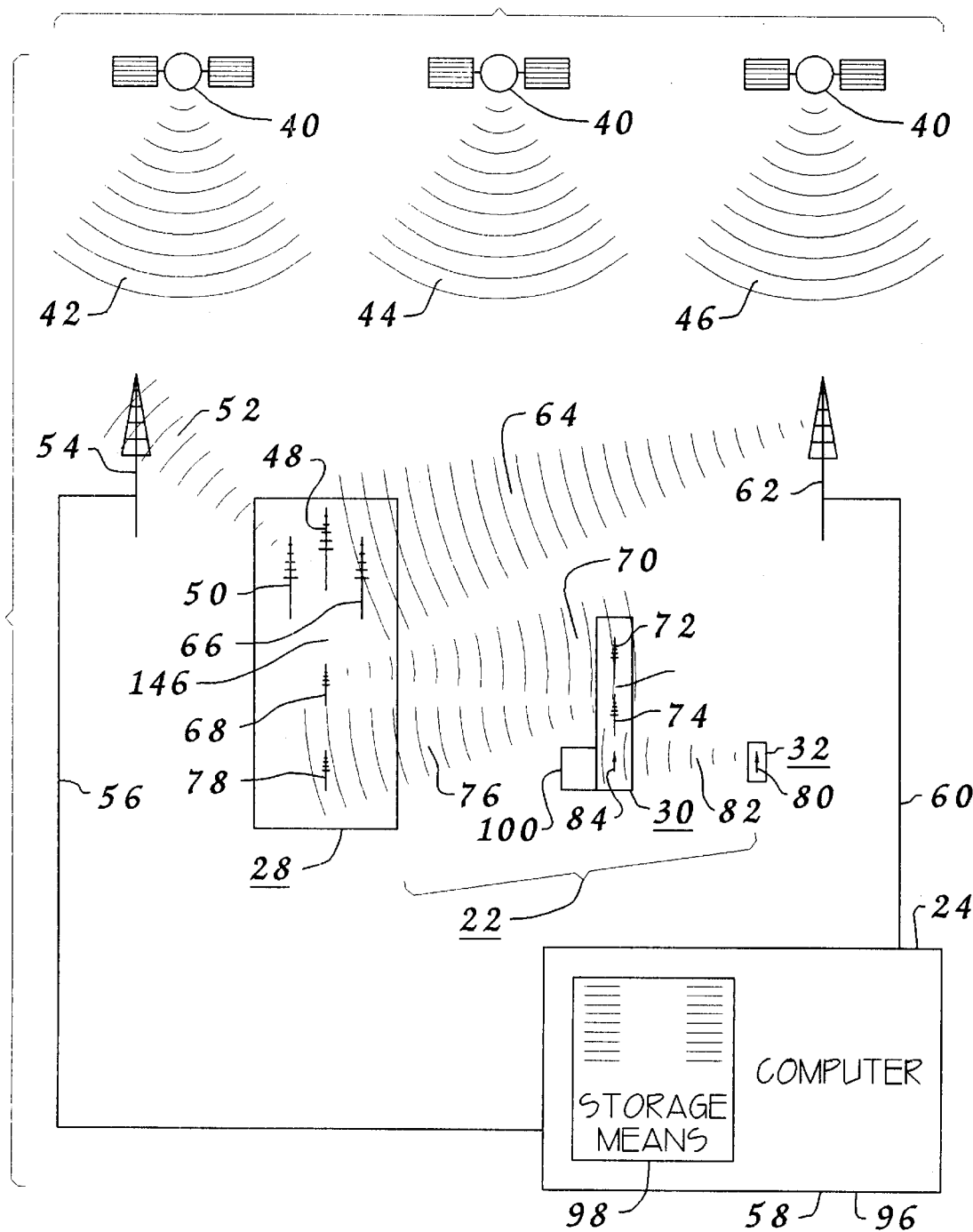
FIG. 1 is an illustration of an embodiment of a system having features of the present invention.

Reference is hereafter made to the drawings where like reference numerals refer to like parts throughout the various views.

Overview

Systems having features of the present invention may perform several important tasks. Each system will have a device for each mobile monitored person, no mobile monitored persons shown in any of the various views, which will monitor at least one bodily function of the respective mobile monitored person. Additionally, structures will exist to selectively provide for an intervention. Such interventions are exampled by a medical intervention in response to a medical crisis in the health of the mobile monitored person and/or notify an oversight authority in response to the medical crisis and/or identify a locational reference indicative of a locational position of the mobile monitored person and/or provide for other intervention as exampled by delivering a low voltage shock, delivering an audio warning or limiting access to select locations to alter behavior of the monitored person.

FIG. 1 depicts a system 20 comprising a mobile monitored person device 22 and an oversight authority 24 wherein all of the above identified functions may be performed by system 20.

Mobile Monitored Person Devices

Various configurations are possible for devices in the possession of the mobile monitored person. Several of these configurations are more fully described herein. In a first general group a single device in the possession of the mobile monitored person acts to provide all of the desired functions which are performed at the mobile monitored person's location. In a second general group multiple devices, each constantly in the immediate possession of the mobile monitored person, act to provide all of the desired functions which are performed at the mobile monitored person's location. In a third general group multiple devices, with at least one of these devices far less restrictively retained about the mobile monitored person than the other device(s), act to provide all of the desired functions which are performed at the mobile monitored person's location. Without regard for the specific configuration deployed, typically at least one sensor type component will be in immediate contact with the mobile monitored person to provide for the below identified requirement of monitoring at least one bodily function of the mobile monitored person.

The mobile monitored person device may take the form of a medical intervention device which is capable of monitoring the mobile monitored person for existence of a medical crisis and initiating an introduction of a medical intervention. The mobile monitored person device may take the form of a medical crisis notification system which is capable of monitoring the mobile monitored person for the existence of the medical crisis and notifying an oversight authority of the status of the mobile monitored person including the location of the mobile monitored person.

Figure 5:
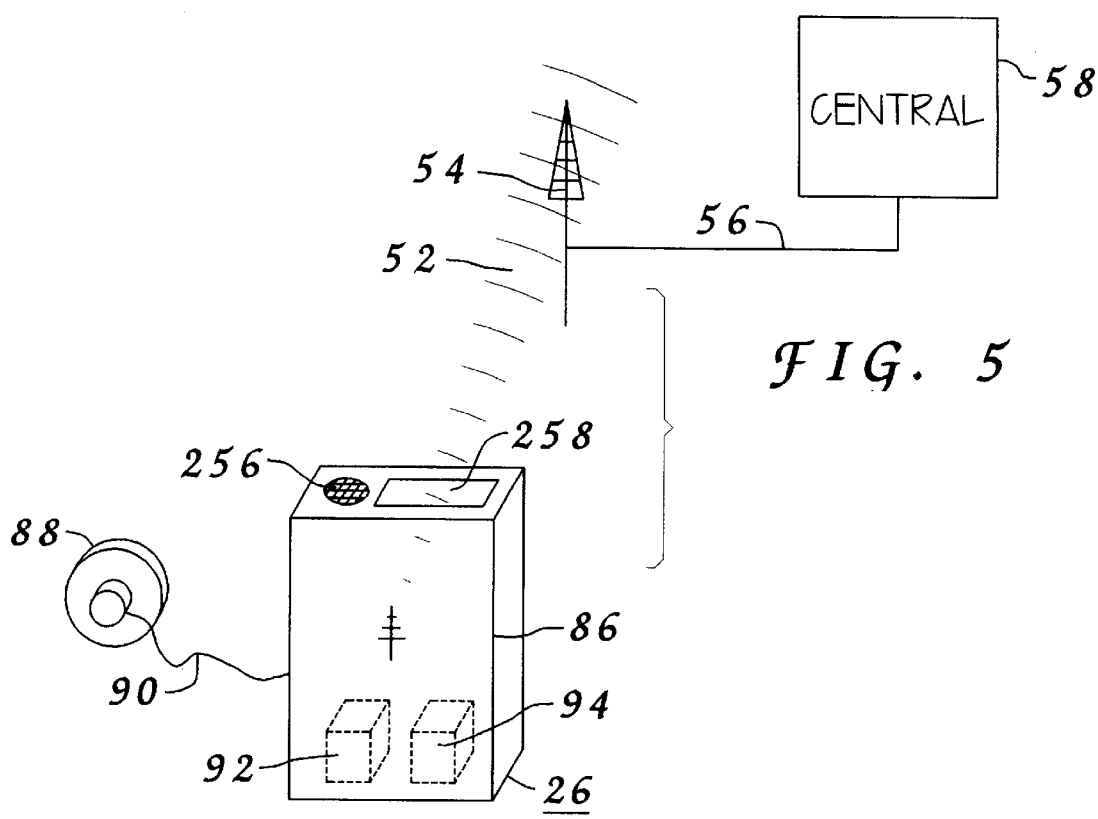
FIG. 5 is an illustration of yet another embodiment of a system having features of the present invention.

FIG. 5 depicts an example of the first general group wherein a medical monitoring device 26 provides all of the desired functions which are performed at the mobile monitored person's location.

FIG. 1 depicts an example of the second general group wherein mobile monitored person device 22 comprises a first component 28, a second component 30 and a third component 32 which cooperate to provide all of the desired functions which are performed at the mobile monitored person's location including medical intervention and oversight notification including identification of the location of the mobile monitored person.

FIG. 2 depicts an example of the third general group wherein a mobile monitored person device 34 which comprises a monitoring device 36 which is retained in immediate possession of the mobile monitored person, and a transportable device 38, which is retained by the mobile monitored person within a predefined range from the mobile monitored person, cooperate to provide all of the desired functions which are performed at the mobile monitored person's location.

In certain configurations various types of communication will occur between various components. The following example depicts several general types of applicable communications. It being understood that while separate components are provided in the various views to perform each distinct function, in many instances a single component may perform multiple functions.

FIG. 1 depicts detached sending units 40 which transmit signals 42, 44 and 46 respectively for subsequent reception by a reception antenna 48 of first component 28 of mobile monitored person device 22. A transmission antenna 50 of first component 28 transmits a signal 52 for reception by a receiving tower 54. Receiving tower 54 transfers signal 52 utilizing a coupling 56 to a central location 58. Central location 58 transmits a signal 64 utilizing a coupling 60 to a transmission tower 62. Transmission tower 62 transmits signal 64 for reception by a reception antenna 66 of first component 28. A short range transmission antenna 68 of first component 28 transmits a signal 70 to a short range reception antenna 72 of second component 30 of mobile monitored person device 22. A short range transmission antenna 74 of second component 30 transmits a signal 76 to a short range reception antenna 78 of first component 28. A short range transmission antenna 80 of third component 32 of mobile monitored person device 22 transmits a signal 82 to a short range reception antenna 84 of second component 30. Alternatively, such transfer may be made utilizing a wired connection. When an implantable monitoring device, as depicted, is employed instead of one of the skin contact type, signal 82 preferably will be transferred utilizing a wireless transfer.

Monitoring Means

Systems having features of the present invention will comprise means to measure at least one bodily function of the mobile monitored person and means to determine if that bodily function is in a crisis range. The term crisis range as used herein refers to a physical condition of the mobile monitored person which is abnormal for the mobile monitored person and which indicates onset, or imminent onset, of a medical problem which may endanger the mobile monitored person.

While it is possible to provide for intermittent monitoring of the bodily function, it is preferable to provide for continual monitoring of at least one bodily function. When multiple bodily functions are being monitored it may be desirable, in order to conserve power, to have a primary bodily function which is continuously monitored and at least one alternative bodily function which is monitored intermittently or only when the primary bodily function exceeds a predetermined range.

The mobile monitored person will have various bodily functions indicative of a general health of the mobile monitored person which may be monitored by electronic equipment, as conventionally known in the art. Many of these bodily functions may be employed by system having features of the present invention. These bodily functions may be employed to determine a status of the mobile monitored person including that current status which would indicate existence of a medical crisis in the health of the mobile monitored person.

Examples of such bodily functions include measurements of operation of the heart including heart rate and uniformity of spacing between beats, blood pressure, respiration rate, measurements of the composition of blood including blood sugar levels and oxygen levels and measurements of activity of the nervous system including brain activity.

The monitoring device may be in contact with the skin of the mobile monitored person, as exampled by a sensor patch, a ring, a bracelet or watch, an anklet or a necklace, or may be implanted.

FIG. 5 depicts medical monitoring device 26 having a body worn device 86, a sensor 88 and a lead 90 connects sensor 88 to body worn device 86. Sensor 88 is retained by an adhesive, not shown, to make contact with the skin of the mobile monitored person.

FIG. 2 depicts mobile monitored person device 34 having two separate components being monitoring device 36 and transportable device 38. Monitoring device 36 makes physical contact with the mobile monitored person during measurement of the respective bodily function. As described elsewhere herein, monitoring device 36 wirelessly communicates with transportable device 38 within a predetermined distance.

FIG. 1 depicts mobile monitored person device 22 having three (3) separate detached components being first component 28, second component 30 and third component 32. First component 28 is exampled by a body worn device such as a belt attachable housing. Second component 30 is exampled by a body contacting medical intervention device which would make physical contact with the monitored person. Third component 32 is exampled by an implantable sensor device which is implanted within the body of the mobile monitored person. Each of the components 28, 30 and 32 communicates, and preferably wirelessly communicates, with at least one of the other components 28, 30 and 32.

Crisis Determining Means

For each mobile monitored person it is possible, based upon various criteria, to establish thresholds for any select bodily function being monitored beyond which the health of the mobile monitored person would be interpreted as being endangered. Such thresholds, depending upon the bodily function being monitored, may involve a set upper limit and/or a set lower limit or may involve a variable threshold which changes depending upon other factors, as exampled by comparison to a measurement of a second bodily function.

The various thresholds, or formulas to arrive at the thresholds, may be stored with the mobile monitored person device, or a component thereof, or may be stored at a fixed location. When stored at the moving location of the mobile monitored person sufficient computational capabilities will exist to permit the desired comparison of the measurement (s) of the bodily function(s) to the threshold(s) to permit a determination to be made if a medical crisis exists or is imminent.

FIG. 5 depicts medical monitoring device 26 having measuring means, in the form of sensor 88, to measure a bodily function of the mobile monitored person, conditional reference storage means, in the form of a storage device 92, containing the predefined threshold, and comparison means, in the form of a central processing unit 94, capable of comparison means to compare the current measurement of the bodily function supplied by sensor 88 and the predefined threshold contained in storage device 92.

FIG. 1 depicts oversight authority 24 positioned at central location 58. Central location 58 has a computer 96 having a storage device 98. Computer 96 receives signal 52 containing measurements of the bodily function of the mobile monitored person from mobile monitored person device 22. Computer 96, in cooperation with storage device 98, has the ability to compare the measurements of the bodily function of the mobile monitored person to a predefined threshold to determine if a medical crisis exists for the mobile monitored person. If this determination occurs computer 96 can activate various responses including directing mobile monitored person device 22 to implement a medical intervention via a medical intervention unit 100 of second component 30 and/or notify emergency personnel to respond to the location of mobile monitored person device 22.

Figure 8:
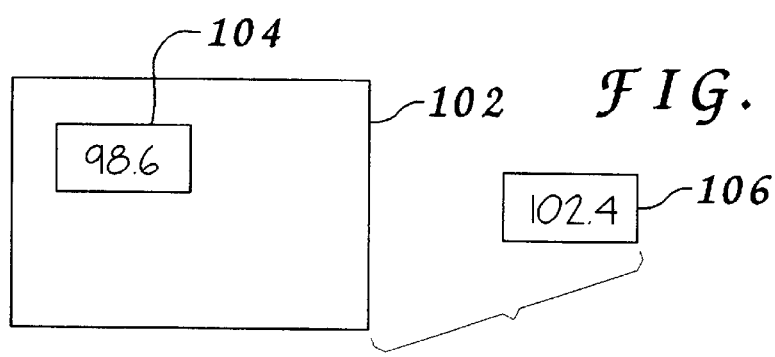
FIG. 8 is a plan view of a representation of a bodily signal conditional database and a representation of a comparative bodily signal reference.

FIG. 8 depicts a bodily signal conditional database 102 having a baseline measurement 104 for a specific bodily function. A comparative bodily signal reference 106 may be compared to baseline measurement 104 utilizing a mathematical computation which would establish an acceptable range to determine if comparative bodily signal reference 106 is within the range, or acceptable, or outside of the range, or unacceptable. In the event that comparative bodily signal reference 106 is unacceptable a predetermined activation of a response by the system may be instituted.

Figure 9:
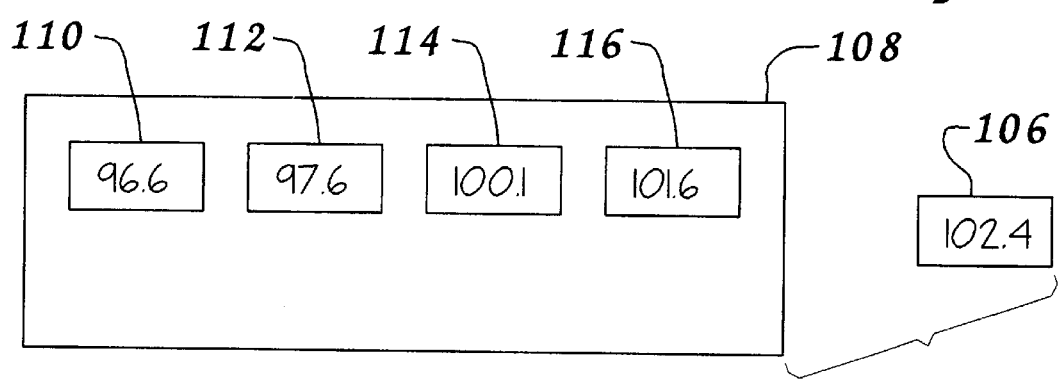
FIG. 9 is a plan view of a representation of a bodily signal conditional database and a representation of a comparative bodily signal reference.

Alternatively, multiple comparative references specific to the bodily function being monitored may exist, as exampled by a bodily signal conditional database 108 as depicted in FIG. 9. In this example, a dangerous lower threshold 110, a warning lower threshold 112, a warning upper threshold 114 and a dangerous upper threshold 116 may be defined within bodily signal conditional database 108. If comparative bodily signal reference 106 reaches, or passes, either warning lower threshold 112 or warning upper threshold 114 a signal would be produced for subsequent action by the overall system or a portion thereof. If comparative bodily signal reference 106 subsequently reaches, or passes, either dangerous lower threshold 110 or dangerous upper threshold 116 a second signal would be produced for subsequent action by the overall system or a portion thereof.

Intervention Means

Such systems may further selectively have means to intervene to attempt to move the bodily function to a safe range or otherwise stabilize the health of the mobile monitored person. During this medical intervention the system, (body), of the mobile monitored person is acted upon when a medical crisis is ongoing in an attempt to stabilize, or otherwise improve, the condition of the mobile monitored person. This intervention may involve the introduction of a medicine or may involve the introduction of an electrical discharge. Introduction of a medicine may involve injection or absorption.

When means exist to provide for a medical intervention it may be desirable to provide the mobile monitored person with a user override wherein the mobile monitored person is notified of an imminent intervention and provided with an option of overriding the medical intervention. When a user override is provided it is a strong desire to provide for notification of the oversight authority of the status of the mobile monitored person where additional medical attention may be summoned if required.

While the present invention is primarily interested in medical intervention as a result of a medical crisis it is possible to provide for routine dispensing of medications to the mobile monitored person utilizing structures of the mobile monitored person device. This may involve timed administration as well as regular administration which is triggered by measurement of a bodily function which does not constitute a medical crisis, as exampled by the routine introduction of insulin for diabetics.

FIG. 1 depicts medical intervention unit 100 of second component 30 of mobile monitored person device 22 and capable of performing a medical intervention upon the monitored person.

FIG. 3 depicts a monitoring device 118 having sensors 120. Additionally, monitoring device 118 has a medication container 122 having a medication, not shown, contained therein. The medication may have a composition which provides for entry into the monitored person by absorption through the skin or which requires injection through the skin. A control device 124 provides for activation of a delivery system 126 when it is required that the medication be introduced into the monitored person. Delivery system 126 provides for micro needles 128, as conventionally known in the art, to be deployed for injection of the medication into the monitored person. Alternatively, a conventional injection needle may be so deployed to provide for entry of the medication. Alternatively, delivery system 126 may release, as exampled by spraying, the medication of an absorbent type onto the skin of the monitored person where the medication may be absorbed for entry into the system of the monitored person.

FIG. 4 depicts a monitoring device 130 having sensors 120. Additionally, monitoring device 130 has a control device 132 and a delivery system 134. Control device 132 may cause activation of delivery system 134 wherein a high voltage electrical shock, as conventionally known in the art, from a power supply 136 may be delivered to the monitored person via a first electrode 138 and a second electrode 140.

FIG. 4 also depicts monitoring device 130 having user notification means, in the form of a speaker 142, and user override means, in the form of a cancellation button 144. When some action, such as oversight notification or medical intervention, is going to be taken in response to readings of a bodily function as taken by monitoring device 130 speaker 142 would notify the mobile monitored person and provide for the mobile monitored person to activate the user override means, cancellation button 144, within a predetermined period of time prior to institution of the action to cancel the action.

Locational Determining Means

Such systems may further selectively have means to determine a locational reference indicative of a locational position of the mobile monitored person. Numerous systems exist, including global positioning systems which rely upon signals from satellites in orbit, to permit determination of a locational reference and many of these may be employed with the present invention.

It is a strong desire to provide locational determining means when outside assistance is required where the mobile monitored person may not be fully capable of providing assistance to direct emergency personnel to the location where the mobile monitored person is. Typically, when locational determining means exist for the mobile monitored person device the oversight authority will be automatically informed of the locational reference indicative of the locational position of the mobile monitored person. This is particularly desirable following a medical intervention where emergency personnel may promptly respond to evaluate the mobile monitored person and ascertain if any additional medical attention is required.

Components of the system which determine, or allow for such determination of, the location may either continuously operate or may intermittently perform their task of determining a locational position. The use of intermittent determination of location provides for a power savings over continuous operation. Thus, intermittent sampling allows for a smaller and lighter device which must be transported by the mobile monitored person.

Due to weight restrictions it may be desired to provide for housing of some components in a transportable device which will be moved about with the mobile monitored person while providing the mobile monitored person with the ability to move about freely within a predefined radius of the transportable device. This arrangement provides for a minimal amount of weight and volume which must be constantly carried about by the mobile monitored person.

FIG. 1 depicts a plurality of detached sending units 40, in this embodiment being orbital based transmission satellites, and each capable of broadcasting a unique signal 42, 44 and 46 respectively. Utilization of such orbital satellites in positional systems is well known in the art and may readily be employed within the present invention. Signals 42, 44 and 46 are received by reception antenna 48 of first component 28 of mobile monitored person device 22. Signals 42, 44 and 46 most likely will be independently created without input from other components of system 20. System 20 is capable of determining a locational reference 146 indicative of a locational position of mobile monitored person device 22 following performance of mathematical computations. Mobile monitored person device 22 may transfer such signals, along with any distinct signal(s) created by mobile monitored person device 22 which may be required to computate locational reference 146 of mobile monitored person device 22, to central location 58. Alternatively, mobile monitored person device 22 may perform the required mathematical computations and transfer the actual locational reference 146 to central location 58.

Figure 6:
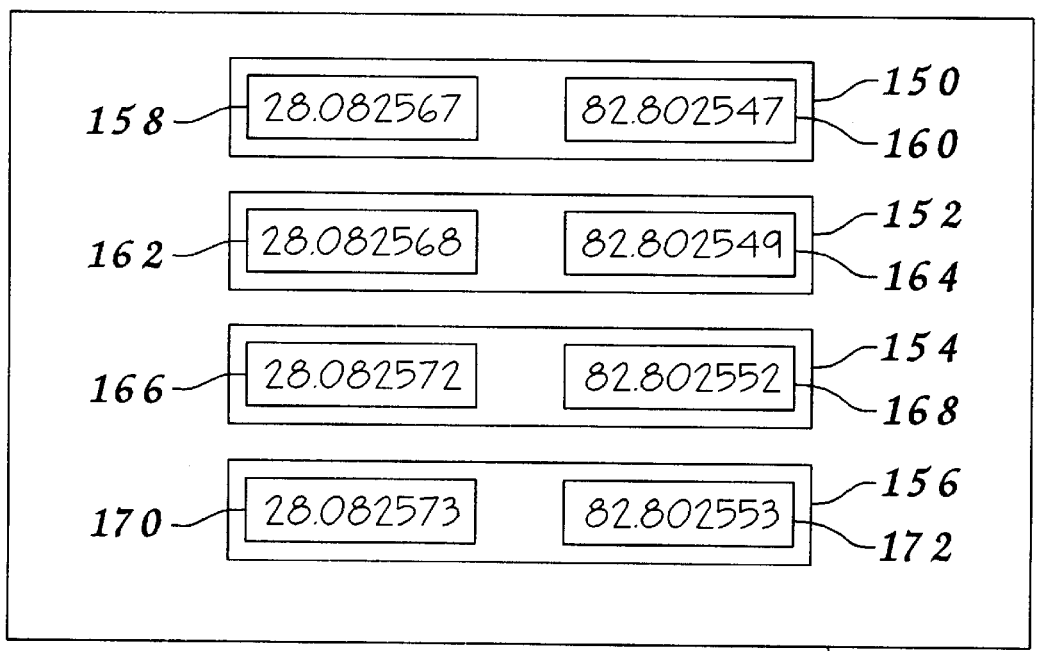
FIG. 6 is a plan view of a representation of a database.

FIG. 6 depicts a database 148 having a series of coordinates 150, 152, 154 and 156. Coordinate 150 comprises a longitudinal reference 158 and a latitude reference 160 which identifies a unique locational position. Coordinate 152 comprises a longitudinal reference 162 and a latitude reference 164 which identifies a unique locational position. Coordinate 154 comprises a longitudinal reference 166 and a latitude reference 168 which identifies a unique locational position. Coordinate 156 comprises a longitudinal reference 170 and a latitude reference 172 which identifies a unique locational position. Various methods may be utilized to create the various coordinates 150, 152, 154 and 156.

FIG. 2 depicts a system 174 including transportable device 38 and monitoring device 36. Monitoring device 36 is securable to a mobile monitored person and therefore is free moving with the mobile monitored person. Transportable device 38 is shown as being moveable by the mobile monitored person using a handle 176. In this embodiment, or variations thereof, the mobile monitored person would be required to remain within a predetermined communication range from transportable device 38 wherein monitoring device 36, attached to the mobile monitored person, and transportable device 38 could communicate wirelessly. This would allow the mobile monitored person to have a free range zone about transportable device 38 within which the mobile monitored person could freely move. When the mobile monitored person desires to moves beyond that range the mobile monitored person would be required to move transportable device 38. This arrangement affords the mobile monitored person reasonable mobility while requiring that a minimum amount of equipment be secured to the mobile monitored person.

Transportable device 38 has a long range reception antenna 178, a long range transmission antenna 180, a short range transmission antenna 182 and a short range reception antenna 184. Monitoring device 36 comprises a short range reception antenna 186 and a short range transmission antenna 188. Short range transmission antenna 182 of transportable device 38 is capable of broadcasting a signal 190 which is received by short range reception antenna 186 of monitoring device 36. Short range transmission antenna 188 of monitoring device 36 is capable of broadcasting a signal 192 which is received by short range reception antenna 184 of transportable device 38. This provides for communication between transportable device 38 and monitoring device 36 while within the free range zone about transportable device 38. Movement beyond this range would result in a lack of communication and result in an indication that the monitored person was in violation of monitoring standards. Warning means, via a speaker 194, would warn the monitored person that this range was being approached while communication still existed, but was determined to be weak.

Transportable device 38 contains structures which enable a determination of a locational reference 196 indicative of its locational position. Transportable device 38 further contains a first locational device 198 while monitoring device 36 contains a second locational device 200. First locational device 198 and second locational device 200 provide for a determination of a general directional indication and a general spacing indication wherein a locational position 202 of monitoring device 36 may be made relative to locational reference 196 of transportable device 38. In such a manner it is possible to make a determination, utilizing methods conventionally known in the art, of locational position 202 (within a reasonable variation) of monitoring device 36 without requiring more complicated equipment located on monitoring device 36.

Figure 7:
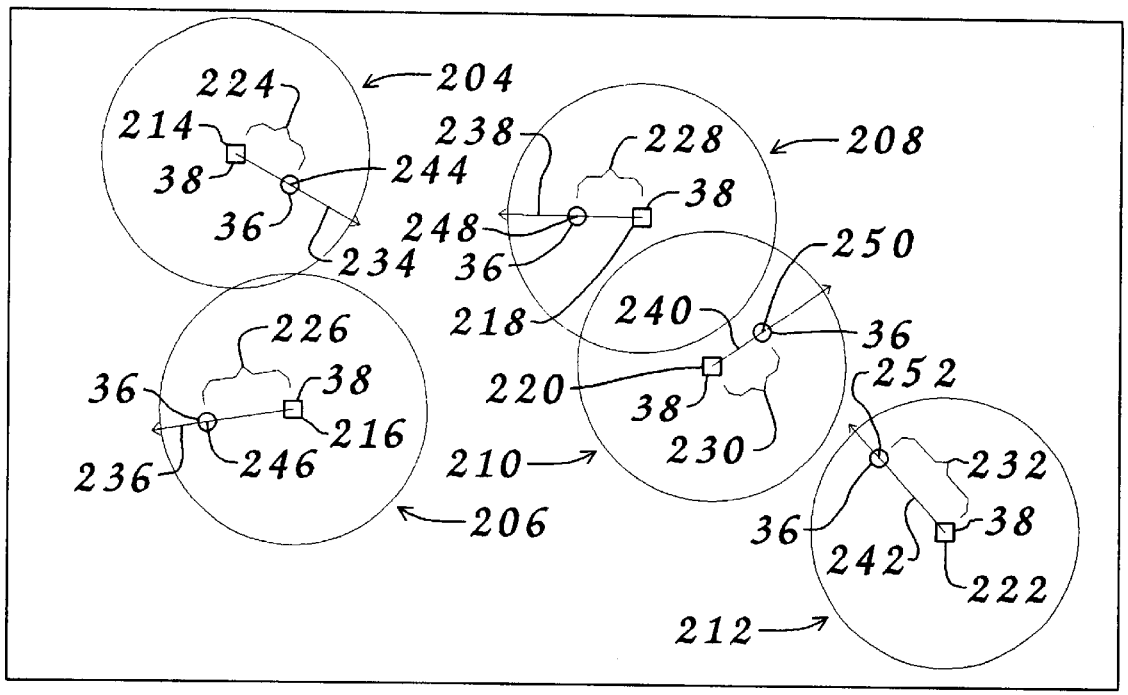
FIG. 7 is a plan view of a block with various locational references distributed therein.

FIG. 7 depicts relative orientations of transportable device 38 and monitoring device 36 as viewed collectively at five (5) distinct time frames represented by five (5) occurrence references 204, 206, 208, 210 and 212. A system, not shown in this view, would acquire information sufficient to allow for a fairly accurate determination of a respective locational reference 214, 216, 218, 220 and 222 of transportable device 38. The system would also acquire information sufficient to allow for a fairly accurate determination of a respective spacing 224, 226, 228, 230 and 232 of monitoring device 36 from transportable device 38. The system would also acquire information sufficient to allow for a fairly accurate determination of a respective orientation 234, 236, 238, 240 and 242 of monitoring device 36 relative to transportable device 38. Utilizing at least this information the system would then be capable of fairly accurately determining locational reference 244, 246, 248, 250 and 252 of monitoring device 36.

Notification Means

As disclosed above each mobile monitored person will have a device in their possession which will monitor at least one bodily function of the mobile monitored person. In certain embodiments of systems this device, or a cooperating device, will receive information from and/or transmit information to an oversight authority. In these instances the oversight authority will utilize a detached receiving unit to receive the information contained within a signal transmitted from the mobile monitored person. Additionally, the oversight authority may have transmission means for transmission of a signal for subsequent reception by the device in the possession of the mobile monitored person.

Ideally, continuous equipment checks of the system, including communication with each of the mobile monitored person devices, ensure the integrity of the overall system. When communication cannot be established with a component of the system a presumption may be made that a malfunction has occurred and oversight personnel may take whatever steps deemed necessary to confirm the status of the well being of the respective mobile monitored person.

Preferably the mobile monitored person device will notify the oversight authority in the advent of a medical crisis involving the mobile monitored person. It is a strong desire to notify the mobile monitored person that such notification has occurred. In a preferred embodiment the mobile monitored person will be so informed immediately prior to such notification to the oversight authority with at least a few seconds to override and cancel such notification if the mobile monitored person so desires.

The transmission of information from the mobile monitoring device to the oversight authority may be continual, intermittent or specific to a detected event. The use of intermittent transmission or specific transmission as a result of a detected event results in a power savings over continuous transmission which enables smaller and lighter components to be deployed. If either of these configurations are deployed it is possible to provide for short term storage of information within the mobile monitoring device for subsequent transmission. It is possible to place various components of the mobile monitoring device in a scheduled sleep mode with either a scheduled wake up or an event inspired wake up.

When communication exists between components carried about with the mobile monitored person and the oversight authority means will exist for a signal to be sent from the mobile monitored person device to the oversight authority. This signal will include information to identify the mobile monitored person and may contain information about the status of the mobile monitored person. This signal may involve direct communication from the mobile monitored person, as exampled by an audio message, to the oversight authority. Additionally, it may be desired to provide means for a signal to be sent from the oversight authority to the mobile monitored person device. This signal will include information to confirm the identity of the mobile monitored person and may contain directions for components of the mobile monitored person device to perform certain functions. Alternatively, this signal may contain information for subsequent reception by the mobile monitored person, either audio or visual.

It is a strong desire to provide for a help button on the mobile monitored person device where the mobile monitored person may summon assistance. Such assistance may be of a medical nature or of some other type of assistance as exampled by in response to being a victim of a crime.

Additionally, it is possible to provide the mobile monitored person with an input device on the mobile monitored person device which allows the mobile monitored person to enter information for subsequent transfer to the oversight authority. Examples of such information may include confirmation that the mobile monitored person took a certain medicine including recording the time that the medicine was taken. This provides for confirmation that all prescribed medications have been properly taken. The mobile monitored person device may. inform the mobile monitored person that it is time to take a scheduled medication or that a scheduled medication is past due to be taken. Such information, including recording of consumption of non prescribed or over the counter medications, may be extremely important to medical personnel in the event of a medical crisis where the mobile monitored person may not be capable of accurately, if at all, personally informing the medical personnel of the consumption of such medications.

FIG. 1 depicts system 20 wherein mobile monitored person device 22 sends signal 52 for subsequent reception by oversight authority 24 containing information indicative of locational reference 146 of mobile monitored person device 22 and information about a status of the mobile monitored person as gathered by third component 32 of mobile monitored person device 22. Signal 52 may also contain information about any medical intervention instituted by medical intervention unit 100 of second component 30 of mobile monitored person device 22 upon the mobile monitored person.

FIG. 2 depicts speaker 194 of monitoring device 36 capable of bi-directional transmission of an audio signal between the mobile monitored person and central location 58. This audio signal provides for direct communication during time of crisis to inform the mobile monitored person of the status of any response initiated by central location 58.

FIG. 2 also depicts a help button 254 which may be activated by the mobile monitored person to summon assistance from central location 58. Activation of help button 254 may invoke communication between the mobile monitored person and central location 58 via speaker 194.

FIG. 5 depicts medical monitored device 26 having an audio output 256 and a LED readout 258. Audio output 256 may give audio notification including specific sounds, programmed verbal announcements or verbal communication from live personnel. Audio output 256 may provide for two way communication between the monitored person and personnel at central location 58. LED readout 258 may give visual notification including text readout.

Preservation of Data

When desired the oversight authority may store select information in a storage device of a computer device as an accessible file. Such a file provides for real time dissimulation of the information or historic preservation of the information. Preferably, such information in the file may be accessed via an internet connection where other interested persons, with proper security approval, may acquire the information.

When historic preservation occurs it may be utilized by medical personnel as a tool to better understand the condition of the mobile monitored person and to better design a treatment for the mobile monitored person. This information may have tremendous diagnostic value even when a medical crisis does not occur.

FIG. 10a depicts a database 260 comprised of a series of three (3) bodily signal references 262, 264 and 266 containing data indicative of blood pressure readings for a monitored person, not shown.

FIG. 10b depicts a database 268 comprised of a series of three (3) bodily signal references 270, 272 and 274 containing data indicative of heart beat rate readings for a monitored person, not shown.

FIG. 10c depicts a database 276 comprised of a series of three (3) bodily signal references 278, 280 and 282 containing data indicative of respiration rate readings for a monitored person, not shown.

FIG. 10d depicts a database 284 comprised of a series of three (3) bodily signal references 286, 288 and 290 containing data indicative of bodily temperature readings for a monitored person, not shown.

FIG. 10e depicts a database 292 comprised of a series of three (3) bodily signal references 294, 296 and 298 containing data indicative of blood oxygen readings for a monitored person, not shown.

FIG. 10f depicts a database 300 comprised of a series of three (3) bodily signal references 302, 304 and 306 containing data indicative of blood alcohol readings for a monitored person, not shown.

Any of the conversion methods conventionally known in the art may be utilized to convert applicable sensor data into respective database 260, 268, 276, 284, 292 or 300. As conventionally known in the art, references may be created and stored which provide for an indication of the time span that each of the bodily signal references refers to.

Dissimulation of Information About Mobile Monitored Person

Information may be dissimulated via an e-mail transmission, via a telephonic transmission or via an internet posting on a web site. This provides for notification of select persons about the status of the mobile monitored person either on a routine basis or when the mobile monitored person is undergoing a medical crisis. In a first example the oversight authority routinely receives information regarding the status of the health of the mobile monitored person and periodically dissimulates that information to allow for reassurance of approved family members and friends as to the well being of the mobile monitored person. In a second example the oversight authority dissimulates information to approved persons only when a medical crisis has occurred along with information indicative of the current status of the mobile monitored person. The current status of the mobile monitored person may include current medical condition, medical treatment given, current location of the mobile monitored person and contact information such as medical personnel numbers. Additionally, a list of persons to be contacted may be maintained by the oversight authority and updated to indicate which persons have been notified and which persons remain to be notified. This information may be provided to approved persons which may then assist in the notification of persons scheduled to be notified which have not previously been automatically notified.

When the information about the mobile monitored person is dissimulated other information may be included. Examples of such information includes maps indicating the location of the mobile monitored person, maps indicating the intended destination of the mobile monitored person and contact names and associated information such as phone numbers.

FIG. 11 depicts an e-mail transmission 308 containing various information 310 and advising Ms. Sue Smith that her father, Mr. John Smith has suffered a mild heart attack at 9:43 A.M.; that he has been transported to and admitted to General Hospital in Anycity Fla., that he is in stable condition, out of danger and resting comfortably, that he will be held for testing for at least two days. Contact information is given in the form of a general phone number for the hospital, a telephone number at the nursing station at the hospital and the name and telephone number of the attending doctor. Information regarding visiting hours is also listed.

FIG. 12 depicts a web site 312, accessible following proper password confirmation of authorization to view the data, containing various information and, following passage through various pages 314, certain information about a monitored person may be accessed.

Referring back to FIG. 2, central location 58 may transmit via a phone line 316 to move the various information to the internet.

Monitoring Examples

The mobile monitored person may freely move about their daily activities while being monitored by systems having features of the present invention. Such monitoring may also occur while the monitored person sleeps in a stationary position. The mobile monitored person having limited mobility may also be monitored by such systems. Examples of such persons include residents of retirement communities as well as nursing homes and persons being treated in hospitals. The persons residing in nursing homes may particularly benefit from use of monitoring devices having features of the present invention. When a medical crisis develops the system may immediately notify the staff including specifics about the condition of the monitored person and an exact location whether that be in a specific room or in a specific location within a hallway. The system may monitor many persons and activate an alert or simply store time and location data when two monitored persons are together. One example of this involves a system which monitors residents of a facility to keep track of the various residents. In this instance a notification may be made to supervisory personnel when a first monitored person enters a room of a second monitored person including notification of the presence in the room, or lack thereof, of the resident assigned to the room. Systems of the present invention are ideally suited to prevent residents of facilities from wandering off while confused and assist in expedient location of any residents which manage to wander off.

With respect to the above description then, it is to be realized that the optimum dimensional relationships for the parts of the invention, to include variations in size, material, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medical intervention device comprising:
   a) measuring means to provide for a measuring of a bodily function of a mobile monitored person;
   b) crisis determining means to provide for making a determination if the bodily function of the mobile monitored person as measured by the measuring means has reached a predetermined threshold, the predetermined threshold indicative of a medical crisis within a health of the mobile monitored person, the crisis determining means producing a signal in response to the bodily function reaching the predetermined threshold;
   c) intervention means to provide for a medical intervention directed to the mobile monitored person in response to the signal produced by the crisis determining means;
   d) timing means to provide for a delaying of an activation of the medical intervention of the intervention means following production of the signal by the crisis determining means a predetermined measurement of time;
   e) signaling means to provide for a notification of the mobile monitored person that the crisis determining means has produced the signal and that the timing means is delaying activation of the medical intervention of the intervention means the predetermined measurement of time;
   f) cancellation means to provide for the mobile monitored person to cancel the medical intervention of the intervention means during the predetermined measurement of time.

2. The medical intervention device defined in claim 1 further comprising:
   a) locational determining means to provide for making a determination of a locational reference indicative of a locational position of the mobile monitored person;
   b) transmitting means to provide for a transmission of a signal from the locational position of the mobile monitored person to an oversight authority.

3. The medical intervention device defined in claim 1 further comprising:
   a) transmitting means to provide for a transmission of a signal;
   b) notification means to provide for a notification of the oversight authority when the crisis determining means produces the signal indicative of the bodily function reaching the predetermined threshold.

4. The medical intervention device defined in claim 3 wherein the notification of the oversight authority by the notification means further comprising:
   a) a confirmation of a delivery the medical intervention to the mobile monitored person;
   b) a current status of the bodily function of the mobile monitored person as currently measured by the measuring means.

5. The medical intervention device defined in claim 1 further comprising transmitting means to provide for a transmission of a signal, the signal containing information indicative of a status of the mobile monitored person;
   and wherein the signal is received by a detached receiving unit and the information indicative of the status of the mobile monitored person is stored in an accessible file on a storage device of a computer device;
   and wherein the accessible file may be accessed via an internet connection wherein the information indicative of the status of the mobile monitored person may be acquired via the internet connection.

6. The medical intervention device defined in claim 1 wherein the medical intervention of the intervention means further comprises an introduction of an electrical discharge into a system of the mobile monitored person.

7. A medical crisis notification system to provide for alerting an oversight authority of an existence of a medical crisis in a health of a mobile monitored person while the mobile monitored person is mobile during activities of daily living, the medical crisis notification system comprising:
   a) a mobile monitoring device to provide for a monitoring of a bodily function of the mobile monitored person, the mobile monitoring device producing a signal indicative of a measurement of the bodily function being monitored;

b) conditional reference storage means to provide for a storing of a conditional reference, the conditional reference having at least a crisis limit for the bodily function being monitored by the mobile monitoring device, the crisis limit indicative of the medical crisis of the health of the mobile monitored person;

c) comparison means to provide for a comparison of the signal indicative of the measurement of the bodily function as monitored by the mobile monitoring device with the conditional reference to determine if the bodily function has met the crisis limit and therefore indicative of the medical crisis of the health of the mobile monitored person;

d) locational determining means to provide for making a determination of a locational reference indicative of a locational position of the mobile monitored person during a free ranging movement of the mobile monitored person during activities of daily living;

e) transmitting means to provide for a transmission of a signal from the locational position of the mobile monitored person to the oversight authority;

f) notification means to provide for a notification of the oversight authority utilizing the signal of the transmitting means when the comparison of the comparison means indicates that the signal produced by the mobile monitoring device has met the crisis limit of the conditional reference of the conditional reference storage means, the notification of the oversight authority including at least the locational reference indicative of the locational position of the mobile monitored person.

8. The medical crisis notification system defined in claim 7 further comprising:

a) crisis determining means to provide for making a determination if the bodily function of the mobile monitored person as measured by the measuring means has reached a predetermined threshold, the predetermined threshold indicative of the medical crisis within the health of the mobile monitored person, the crisis determining means producing a signal in response to the bodily function reaching the predetermined threshold;

b) intervention means to provide for a medical intervention directed to the mobile monitored person in response to the signal produced by the crisis determining means.

9. The medical crisis notification system defined in claim 7 further comprising mobile monitored person activation means to provide for the mobile monitored person to initiate the notification means wherein the notification of the oversight authority occurs and wherein the notification of the oversight authority also includes information indicative of an activation of the mobile monitored person activation means.

10. The medical crisis notification system defined in claim 7 wherein the notification of the notification means involves the transmission of at least some information contained in the signal of the transmitting means via an e-mail transmission to the oversight authority.

11. The medical crisis notification system defined in claim 7 wherein the notification of the notification means involves the transmission of at least some information contained in the signal of the transmitting means via a telephonic transmission to the oversight authority.

12. The medical crisis notification system defined in claim 7 wherein the signal transmitted by the transmitting means is received by a detached receiving unit and the information indicative of the status of the mobile monitored person is stored in an accessible file on a storage device of a computer device;

and wherein the accessible file may be accessed via an internet connection wherein the information indicative of the status of the mobile monitored person may be acquired via the internet connection.

13. A medical crisis notification system to provide for alerting an oversight authority of an existence of a medical crisis in a health of a mobile monitored person, the medical crisis notification system device comprising:

a) a monitoring assembly comprising:
1) a mobile monitored person device to be moved about with the mobile monitored person during movement of the mobile monitored person, the mobile monitored person device comprising transmitting means to provide for a transmission of a signal;
2) a mobile companion device which is moveable by the mobile monitored person and about which the mobile monitored person may freely move wherein the mobile monitored person remains within a predefined spacing about the mobile companion device, the mobile companion device comprising:
   i) receiving means to provide for a reception of the signal produced by the transmitting means of the mobile monitored person device;
   ii) transmitting means to provide for a transmission of a signal;
3) monitoring means to provide for a monitoring of a bodily function of the mobile monitored person, the monitoring means producing a signal indicative of a measurement of the bodily function being monitored;

b) conditional reference storage means to provide for a storing of a conditional reference, the conditional reference having at least a crisis limit for the bodily function being monitored by the mobile monitoring device, the crisis limit indicative of the medical crisis of the health of the mobile monitored person;

c) comparison means to provide for a comparison of the signal indicative of the measurement of the bodily function as monitored by the monitoring means of the monitoring assembly with the conditional reference to determine if the bodily function has met the crisis limit and therefore indicative of the medical crisis of the health of the mobile monitored person;

d) locational determining means to provide for producing information from which a locational reference may be created indicative of a locational position of the mobile companion device;

e) computational means to provide for determining a locational position of the mobile monitored person device utilizing at least:
1) the information of the locational determining means indicative of the locational position of the mobile companion device;
2) the signal from the mobile monitored person device received by the receiving means of the mobile companion device;
wherein the locational position of the mobile companion device may be determined then the locational position of the mobile monitored person device is determined based upon a determining of a spacing and an orientation of the mobile monitored person device relative to the mobile companion device, and;

f) conversion means to provide for converting the locational position of the mobile monitored person device to the locational reference for the mobile monitored person;

g) notification means to provide for a notification of the oversight authority utilizing the signal of the transmitting means of the mobile companion device when the comparison of the comparison means indicates that the signal of the measurement of the bodily function produced by the monitoring means of the monitoring assembly has met the crisis limit of the conditional reference of the conditional reference storage means, the notification of the oversight authority including at least the locational reference indicative of the locational position of the mobile monitored person.

14. The medical crisis notification system defined in claim 13 further comprising:

a) crisis determining means to provide for making a determination if the bodily function of the mobile monitored person as measured by the measuring means has reached a predetermined threshold, the predetermined threshold indicative of a medical crisis within a health of the mobile monitored person, the crisis determining means producing a signal in response to the bodily function reaching the predetermined threshold;

b) intervention means to provide for a medical intervention directed to the mobile monitored person in response to the signal produced by the crisis determining means.

15. The medical crisis notification system defined in claim 13 wherein:

a) the oversight authority further comprises transmission means to provide for a transmission of a signal, the signal containing information for the mobile monitored person; and b) wherein the monitoring assembly further comprises receiving means to provide for a reception of the signal transmitted from the oversight authority.

16. The medical crisis notification system defined in claim 13 further comprising historic preservation means to provide for a storage of the measurements of the bodily function of the mobile monitored person, the historic preservation means comprising a reception by a detached receiving unit of the signal containing the measurement of the bodily function being monitored and transmitted by the transmitting means of the mobile companion device wherein information contained in the signal is subsequently stored in a file on a storage device of a computer device.

17. The medical crisis notification system defined in claim 13 further comprising crisis historic preservation means to provide for a storage of the measurements of the bodily function of the mobile monitored person during the medical crisis, the crisis historic preservation means comprising a reception by a detached receiving unit of the signal containing the measurement of the bodily function being monitored during the medical crisis and transmitted by the transmitting means of the mobile companion device wherein information contained in the signal is subsequently stored in a file on a storage device of a computer device.

18. The medical crisis notification system defined in claim 13 wherein the mobile companion device further comprises short range transmitting means to provide for a transmission of a weak signal; and wherein the mobile monitored person device of the monitoring assembly further comprises short range receiving means to provide for a reception of the weak signal produced by the short range transmitting means of the mobile companion device wherein a bidirectional communication link exists between the mobile companion device of the monitoring assembly and the mobile monitored person device of the monitoring assembly.

* * * * *